US00PP19158P2

(12) United States Plant Patent
Heffron

(10) Patent No.: US PP19,158 P2
(45) Date of Patent: Aug. 26, 2008

(54) ***IMPATIENS* PLANT NAMED 'BALCELAPT'**

(50) Latin Name: *Impatiens hawkeri*
Varietal Denomination: Balcelapt

(75) Inventor: Leslie Heffron, Hickory, NC (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/973,970

(22) Filed: Oct. 11, 2007

(51) Int. Cl.
*A01H 5/00* (2006.01)

(52) U.S. Cl. ..... Plt./317
(58) Field of Classification Search ..... Plt./317
See application file for complete search history.

(56) References Cited

PUBLICATIONS

Canada Plant Breeders' Rights application No. 07–5871 filed Apr. 12, 2007. Published information from Canada Plant Breeders' Rights Office web site attached.

European Plant Breeders' Rights application No. 2007/2156 filed Oct. 1, 2007—not published when this IDS was prepared.

*Primary Examiner*—Annette H Para
(74) *Attorney, Agent, or Firm*—Audrey Charles

(57) ABSTRACT

A new and distinct cultivar of *Impatiens* plant named 'Balcelapt', characterized by its single type medium and light orange bicolored flowers, dark green-colored foliage, and vigorous, upright-mounded growth habit.

1 Drawing Sheet

Latin name of genus and species of plant claimed: *Impatiens hawkeri.*
Variety denomination: 'Balcelapt'.

BACKGROUND OF THE INVENTION

The present invention relates to a new and distinct cultivar of *Impatiens* plant botanically known as *Impatiens hawkeri* and hereinafter referred to by the cultivar name 'Balcelapt'.

The new cultivar originated in a controlled breeding program in Arroyo Grande, Calif. during September 2003. The objective of the breeding program was the development of *Impatiens* cultivars with numerous large flowers, attractive flower coloration, and a freely basal branching growth habit.

The new *Impatiens* cultivar is the result of cross-pollination. The female (seed) parent of the new cultivar is Celebration Bright Salmon 'Balcelbrisal', U.S. Plant Pat. No. 17,839, characterized by its single type medium salmon-colored flowers, dark green-colored foliage, and upright-mounded growth habit. The male (pollen) parent of the new cultivar is Infinity Orange 'Visinforan', U.S. Plant Pat. No. 16,247, characterized by its single type medium orange-colored flowers, dark green-colored foliage, and upright-rounded growth habit. The new cultivar was discovered and selected as a single flowering plant within the progeny of the above stated cross-pollination during March 2004 in a controlled environment at Arroyo Grande, Calif.

Asexual reproduction of the new cultivar by terminal stem cuttings since March 2004 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcelapt' as a new and distinct cultivar of *Impatiens* plant:

1. Single type, medium and light orange bicolored flowers;
2. Dark green-colored foliage; and
3. Vigorous, upright-mounded growth habit.

Plants of the new cultivar differ from plants of the female and male parents primarily in flower color.

Of the many commercially available *Impatiens* cultivars known to the inventor, the most similar in comparison to the new cultivar is Super Sonic Salmon Ice, not patented. However, in side by side comparisons, plants of the new cultivar differ from plants of Salmon Ice in the following characteristics:

1. Plants of the new cultivar have a darker foliage than plants of Salmon Ice; and
2. Plants of the new cultivar have a flower color different from plants of Salmon Ice.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcelapt'. The plants were grown in 4.5 inch pots for 11 weeks in a greenhouse at West Chicago, Ill.

DETAILED BOTANICAL DESCRIPTION

Figure 1:
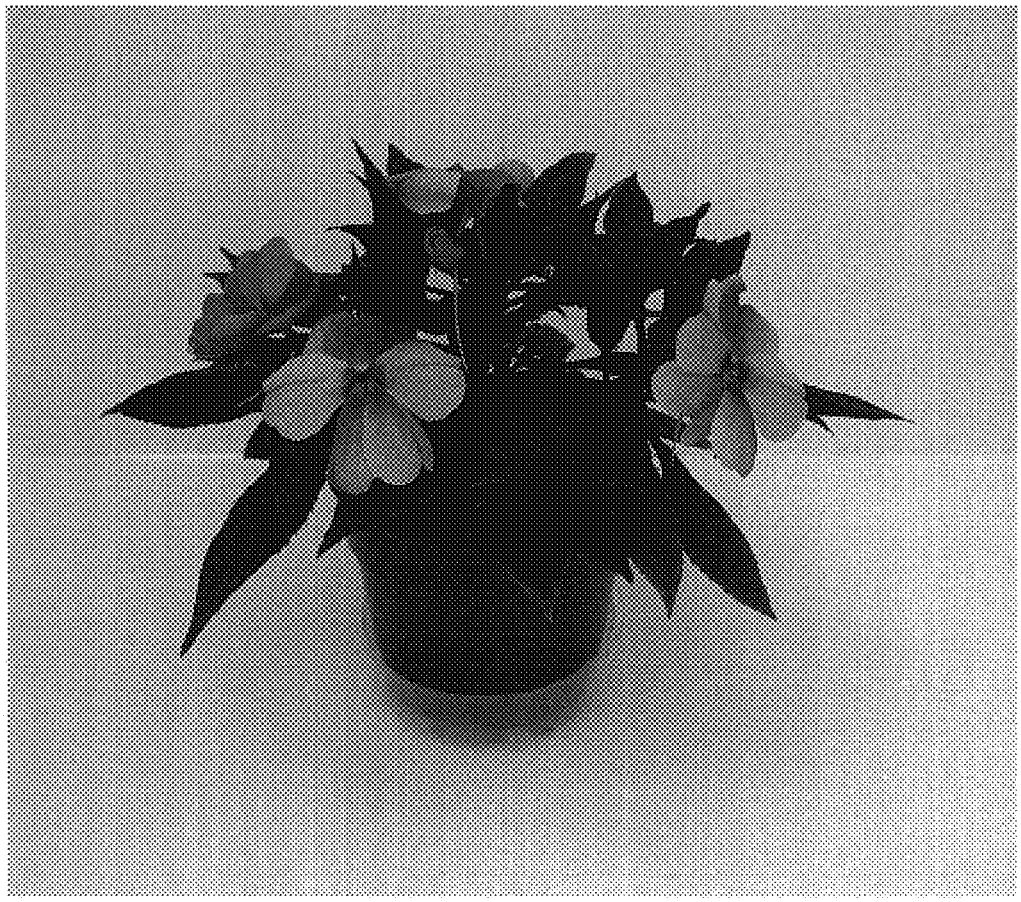
FIG. 1 illustrates a side view of the overall growth and flowering habit of 'Balcelapt'.
Figure 2:
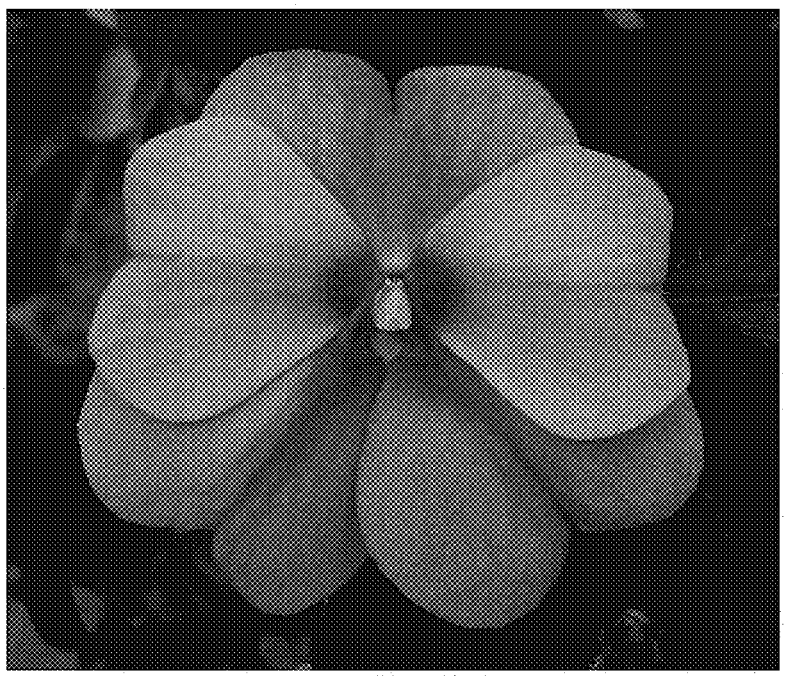
FIG. 2 illustrates a close-up view of an individual flower of 'Balcelapt'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 19, 2007 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 11 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens hawkeri* cultivar Balcelapt.

Parentage:

*Female parent.*—Celebration Bright Salmon 'Balcelbrisal', U.S. Plant Pat. No. 17,839.

*Male parent.*—Infinity Orange 'Visinforan', U.S. Plant Pat. No. 16,247.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 7 to 9 weeks from a rooted cutting to finish in a 10 cm pot.

*Growth habit and general appearance.*—Vigorous, upright-mounded.

*Size.*—Height from soil level to top of plant plane: Approximately 12.3 cm. Width: Approximately 23.6 cm.

*Branching habit.*—Freely basal branching. Quantity of main branches per plant: Approximately 5.

*Branch.*—Strength: Strong. Length: Approximately 8.1 cm. Diameter at central internode: Approximately 5.0 mm. Length of central internode: Approximately 1.8 cm. Texture: Glabrous. Color of young and mature stems: 144A with an overlay of 187B.

Foliage description:

*General description.*—Quantity of leaves per main branch: Approximately 8. Fragrance: None. Form: Simple. Arrangement: In whorls of 3 to 5 leaves.

*Leaves.*—Aspect: Petiole is at an acute angle to stem and leaf blade is perpendicular to stem. Shape: Elliptic. Margin: Serrate, ciliate. Apex: Acuminate. Base: Attenuate. Venation pattern: Pinnate. Length of mature leaf at center of stem: Approximately 8.8 cm. Width of mature leaf at center of stem: Approximately 2.8 cm. Texture of upper surface: Glabrous. Texture of lower surface: Sparsely pubescent on venation. Color of upper surface of young foliage: 139A with venation of 187B. Color of lower surface of young and mature foliage: 191A with an overlay of N187C and venation of 187B. Color of upper surface of mature foliage: 139A with venation of 187C.

*Petiole.*—Length: Approximately 1.9 cm. Diameter: Approximately 3.0 mm. Texture: Glabrous. Color: 187C.

Flowering description:

*Flowering habit.*—'Balcelapt' is freely flowering under outdoor growing conditions with substantially continuous blooming from spring through autumn and year-round in greenhouse environment.

*Lastingness of individual flower on the plant.*—Approximately 5 to 7 days.

Flower description:

*General description.*—Type: Single. Quantity per plant: Approximately 3. Fragrance: None.

*Bud.*—Rate of opening: Generally takes 3 to 4 days for bud to progress from first color to fully open flower. Quantity showing color per plant: Approximately 1.

*Bud just before opening.*—Shape: Ovoid. Length: Approximately 1.8 cm. Diameter: Approximately 1.5 cm. Color: 44A.

*Corolla.*—Shape: Round, cupped when first open with petals turning downward with age. Width: Approximately 6.8 cm. Depth: Approximately 1.2 cm. Borne: Above and below foliage.

*Petals.*—Quantity: 5. Shape: Obovate. Aspect: Flat. Appearance: Iridescent. Margin: Entire. Apex: Emarginate. Base of upper petal: Truncate. Base of lateral and lower petals: Attenuate. Length of upper petal: Approximately 3.0 cm. Width of upper petal: Approximately 4.3 cm. Length of lateral petals: Approximately 3.2 cm. Width of lateral petals: Approximately 3.4 cm. Length of lower petals: Approximately 3.8 cm. Width of lower petals: Approximately 4.1 cm. Texture of upper and lower surfaces: Glabrous. Color of upper surface when first open: 39C with 41A at center of all petals, although less prominent on lateral petals. Lateral and lower petals have a base of N66B forming an "eye". Color of lower surface when first open: Closest to 41D with midvein of N66B. Color of upper surface when fully open: 39C with 41B at center of all petals, although less prominent on lateral petals. Lateral and lower petals have a base of N66B forming an "eye". Color of lower surface when fully open: Closest to 41D with midvein of N66C.

*Spur.*—Quantity: 1 per flower. Length: Approximately 4.7 cm. Diameter at tip: Approximately 1.0 mm. Diameter at base: Approximately 3.0 mm. Texture: Glabrous. Color: 145C with tip of 145A.

*Peduncle.*—Strength: Strong. Aspect: Acute angle to stem. Length: Approximately 3.4 cm. Diameter: Approximately 2.0 mm. Texture: Glabrous. Color: 145A.

*Sepals.*—Quantity per flower: 4, with one fused to base of upper petal. Shape of lateral sepals: Ovate. Shape of lower sepal: Ovate. Apex of all sepals: Acuminate. Length of lateral sepals: Approximately 1.5 cm. Width of lateral sepals: Approximately 5.0 mm. Length of lower sepal: Approximately 1.7 cm. Width of lower sepal: Approximately 1.2 cm. Texture of upper and lower surfaces of all sepals: Glabrous. Color of lateral sepals: 145D with an overlay of 187B and tip of 187A. Color of lower sepal: Closest to N66D with tip of 187A.

*Reproductive organs.*—Androecium: Stamen quantity: 5 per floret, fused around pistil at apex. Anther shape:

Hooded. Anther length: Approximately 3.0 mm. Anther color: N155B. Filament color: N155B with an overlay of N66B. Pollen amount: Scarce. Pollen color: 155D. Gynoecium: Pistil quantity: 1 per flower. Pistil length: Approximately 5.0 mm. Stigma shape: 5-pointed star. Stigma color: 187D. Style color: 187A. Ovary texture: Glabrous. Ovary color: 144A with speckles of 187B.

Seed and fruit production: Neither seed nor fruit production has been observed.

Disease and pest resistance: Resistance to pathogens and pests common to New Guinea *Impatiens* has not been observed.

What is claimed is:

1. A new and distinct cultivar of *Impatiens* plant named 'Balcelapt', substantially as herein shown and described.

* * * * *